United States Patent
Kubo et al.

(10) Patent No.: US 11,234,596 B2
(45) Date of Patent: Feb. 1, 2022

(54) INFORMATION PROCESSING DEVICE AND RECEIVING METHOD

(71) Applicants: OMRON HEALTHCARE CO., LTD., Muko (JP); OMRON Corporation, Kyoto (JP)

(72) Inventors: Nobuo Kubo, Kyoto (JP); Toru Deno, Kyoto (JP); Hideki Kondo, Kyoto (JP)

(73) Assignees: OMRON HEALTHCARE CO., LTD., Kyoto (JP); OMRON CORPORATION, Kyoto (JP)

( * ) Notice: Subject to any disclaimer, the term of this patent is extended or adjusted under 35 U.S.C. 154(b) by 60 days.

(21) Appl. No.: 16/740,704

(22) Filed: Jan. 13, 2020

(65) Prior Publication Data

US 2020/0146548 A1 May 14, 2020

Related U.S. Application Data

(63) Continuation of application No. PCT/JP2018/028825, filed on Aug. 1, 2018.

(30) Foreign Application Priority Data

Aug. 9, 2017 (JP) .............................. JP2017-154763

(51) Int. Cl.
*H04W 4/80* (2018.01)
*A61B 5/00* (2006.01)
(Continued)

(52) U.S. Cl.
CPC .............. *A61B 5/002* (2013.01); *A61B 5/022* (2013.01); *A61B 5/681* (2013.01); *H04W 4/38* (2018.02); *H04W 4/80* (2018.02)

(58) Field of Classification Search
CPC ........... H04W 4/38; H04W 4/80; H04W 4/70; H04W 52/02; H04W 84/10; H04W 88/02;
(Continued)

(56) References Cited

U.S. PATENT DOCUMENTS

2010/0262664 A1* 10/2010 Brown ................. H04L 47/323
  709/206
2013/0194993 A1* 8/2013 Choi ..................... H04W 72/12
  370/311
(Continued)

FOREIGN PATENT DOCUMENTS

JP   2005-057602 A    3/2005
JP   2013-247549 A    12/2013
(Continued)

OTHER PUBLICATIONS

Official Communication issued in International Patent Application No. PCT/JP2018/028825, dated Oct. 16, 2018.
(Continued)

*Primary Examiner* — Philip J Chea
*Assistant Examiner* — Wuji Chen
(74) *Attorney, Agent, or Firm* — Keating and Bennett, LLP

(57) ABSTRACT

An information processing device according to one aspect of the present invention includes a receiver configured to receive a packet for one-way communication including data from an external device, an application execution unit configured to execute an application which processes the data, and an intermittent reception parameter adjustment unit configured to adjust an intermittent reception parameter for controlling an intermittent reception operation of the receiver so that when the application is operating in a background, a duty ratio of the intermittent reception operation is smaller than when the application is operating in a foreground.

8 Claims, 7 Drawing Sheets

(51) Int. Cl.
*H04W 4/38* (2018.01)
*A61B 5/022* (2006.01)

(58) Field of Classification Search
CPC ......... Y02D 30/70; G06F 13/00; A61B 5/002; A61B 5/681
See application file for complete search history.

(56) References Cited

U.S. PATENT DOCUMENTS

| | | | | |
|---|---|---|---|---|
| 2013/0346991 | A1* | 12/2013 | Murakami | G06F 9/4881 718/102 |
| 2014/0036656 | A1 | 2/2014 | Chou et al. | |
| 2014/0254466 | A1* | 9/2014 | Wurster | H04L 51/18 370/312 |
| 2015/0019686 | A1* | 1/2015 | Backholm | H04W 4/18 709/217 |
| 2015/0123810 | A1* | 5/2015 | Hernandez-Rosas | A61B 5/14503 340/870.02 |
| 2015/0201375 | A1* | 7/2015 | Vannithamby | H04W 12/06 370/311 |
| 2015/0205947 | A1* | 7/2015 | Berman | A61B 5/14532 726/16 |
| 2016/0029149 | A1 | 1/2016 | Morikawa et al. | |
| 2016/0095063 | A1* | 3/2016 | Vigier | H04W 4/80 455/574 |
| 2017/0011210 | A1* | 1/2017 | Cheong | H04W 4/00 |

FOREIGN PATENT DOCUMENTS

| | | |
|---|---|---|
| JP | 2014-006619 A | 1/2014 |
| JP | 2014-216699 A | 11/2014 |
| JP | 2015-526042 A | 9/2015 |
| JP | 5852620 B2 | 2/2016 |
| JP | 2016-534675 A | 11/2016 |
| WO | 2015/042065 A1 | 3/2015 |

OTHER PUBLICATIONS

English translation of Official Communication issued in International Patent Application No. PCT/JP2018/028825, dated Feb. 13, 2020.

* cited by examiner

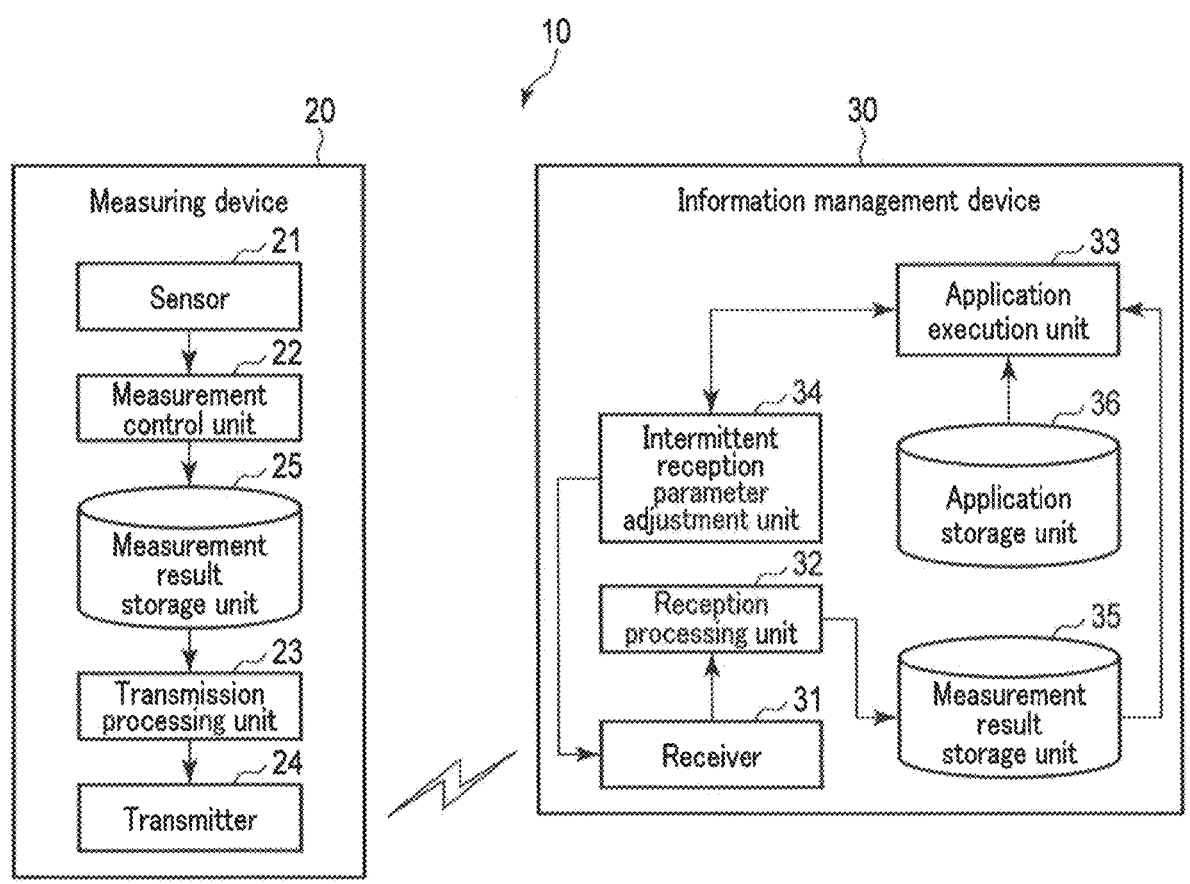
F I G. 1

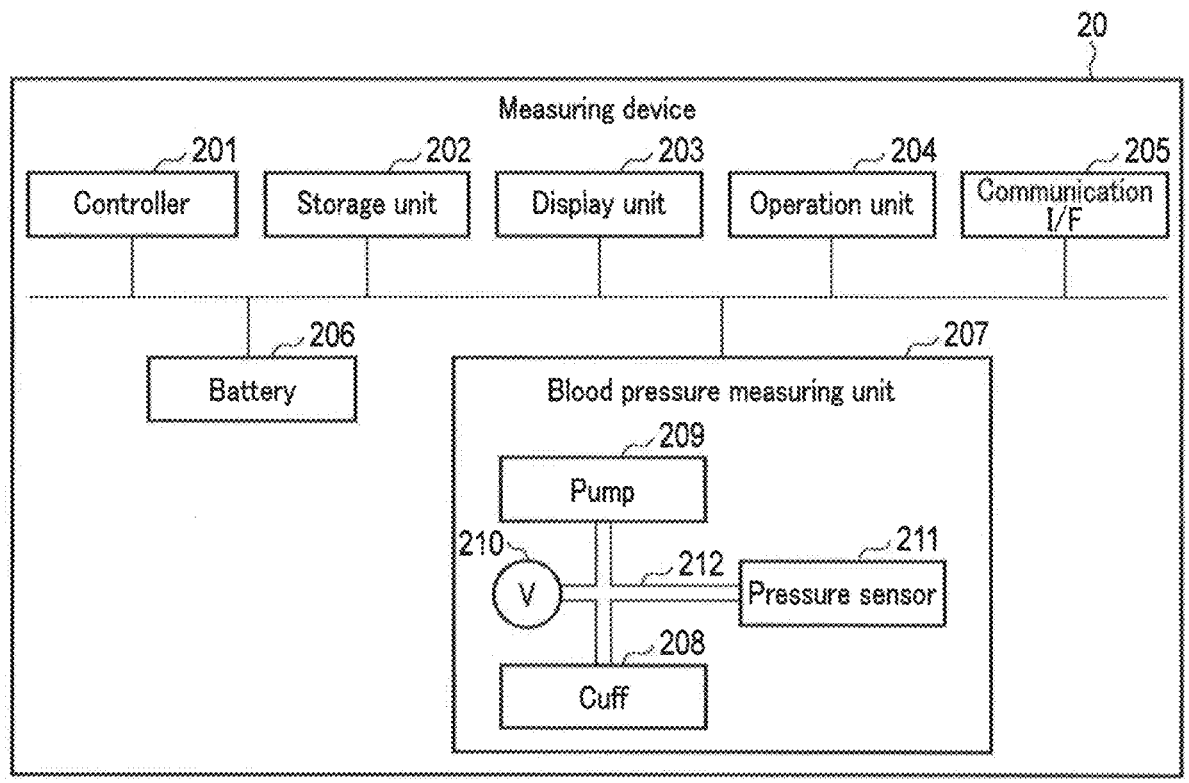
F I G. 2
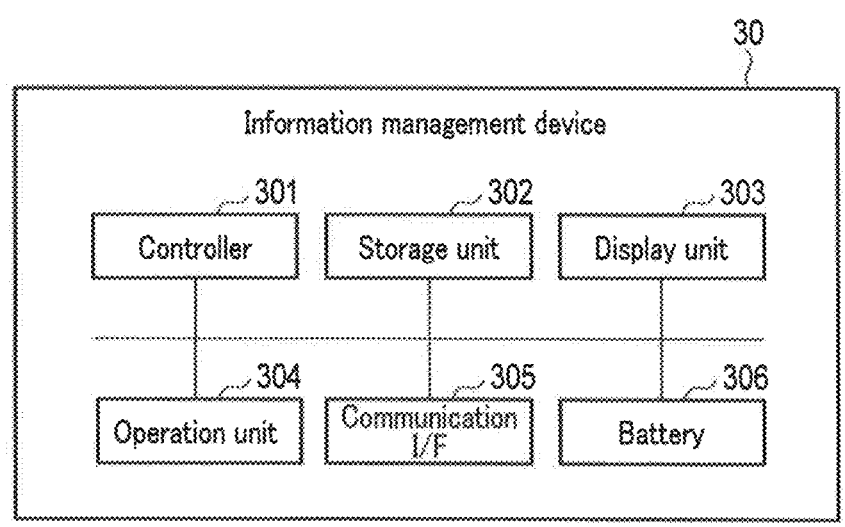
F I G. 3

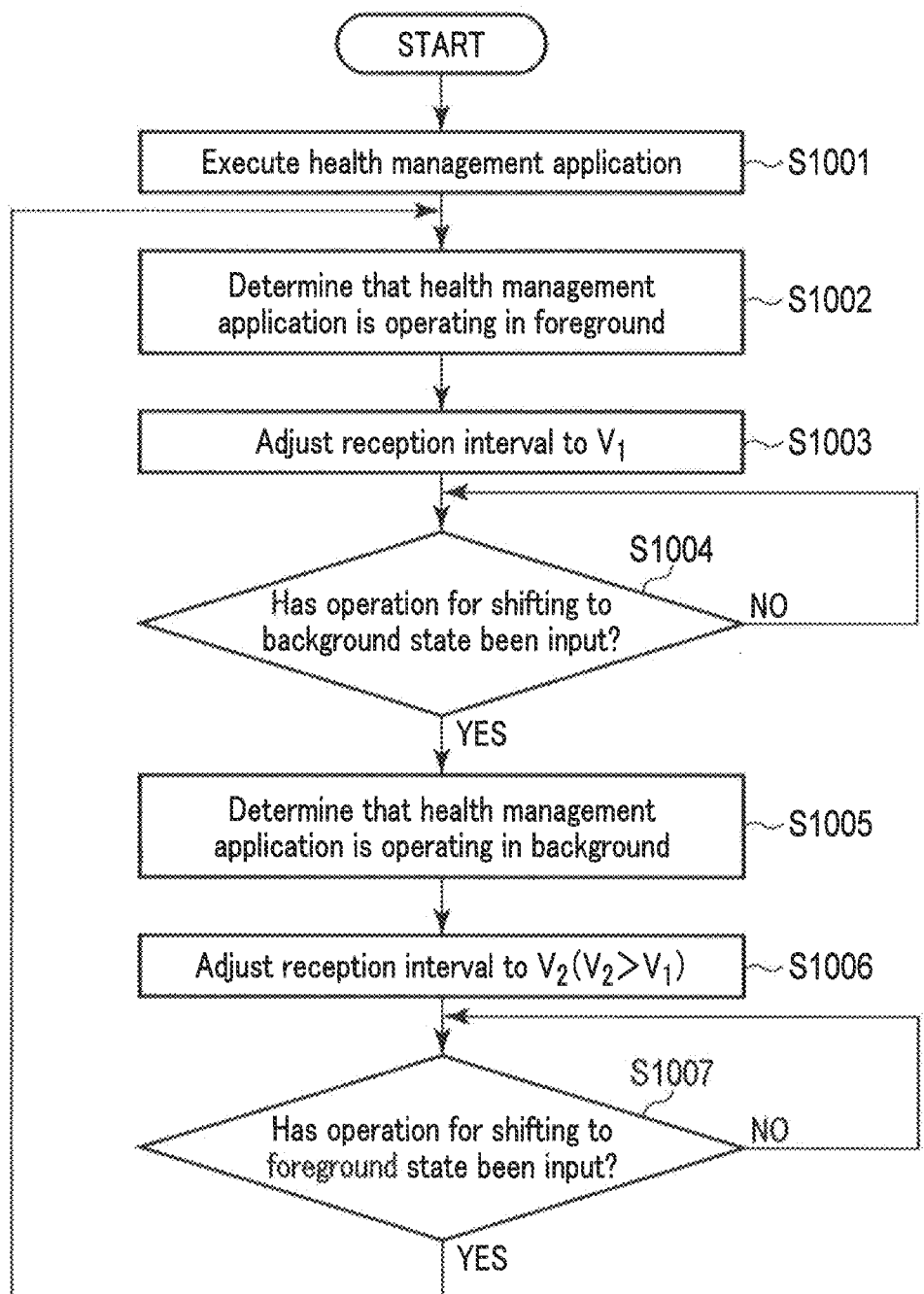
F I G. 10

INFORMATION PROCESSING DEVICE AND RECEIVING METHOD

CROSS-REFERENCE TO RELATED APPLICATIONS

This application is a Continuation application of PCT Application No. PCT/JP2018/028825, filed Aug. 1, 2018 and based upon and claiming the benefit of priority from Japanese Patent Application No. 2017-154763, filed Aug. 9, 2017, the entire contents of all of which are incorporated herein by reference.

FIELD

The present invention relates to a technology for receiving information transmitted from an external device through one-way communication.

BACKGROUND

Blood pressure monitors having a function of transferring blood pressure data to a mobile terminal of a user have been put on the market. Using such a blood pressure monitor, the user can view his or her own blood pressure measurement results on the mobile terminal. Typically, the short-range communication technology such as Bluetooth (registered trademark) is used for transferring blood pressure data. In general, Bluetooth communication can be performed with low power consumption as compared to WLAN (Wireless Local Area Network) communication. Bluetooth version 4.0 is also referred to as BLE (Bluetooth Low Energy), and further reduction of power consumption is attempted as compared to the previous version.

BLE supports two-way communication called connection. However, the connection has a drawback in that the operations that the user is required to perform for pairing are complicated. Furthermore, due to the complicated communication procedures, the connection has the following drawbacks: a compatibility problem is likely to occur between the blood pressure monitor and the mobile terminal; high-performance hardware (processor, memory) is required for both the blood pressure monitor and the mobile terminal; development/evaluation costs are high; and it takes time to start communication.

BLE also supports one-way communication called advertising. Japanese Patent No. 5852620 discloses a technology for including and transmitting optional data in a vacant area of a data field of an advertisement packet for detecting a wireless communication apparatus as a connection partner.

If blood pressure data is transmitted using one-way communication, pairing and subsequent complicated communication procedures are rendered unnecessary, thus solving or alleviating the above-described problems. However, further reduction of power consumption is desired for mobile terminals that receive blood pressure data transmitted through one-way communication.

SUMMARY

The present invention may adopt the following configurations.

An information processing device according to one aspect of the present invention includes a receiver configured to receive a packet for one-way communication, an application execution unit configured to execute an application, and an intermittent reception parameter adjustment unit configured to adjust an intermittent reception parameter for controlling an intermittent reception operation of the receiver so that when the application is operating in a background, a duty ratio of the intermittent reception operation is smaller than when the application is operating in a foreground.

According to the above configuration, the intermittent reception operation of the receiver is controlled so that the duty ratio is smaller when the application is operating in the background than when the application is operating in the foreground. The duty ratio mentioned herein represents a ratio of the duration of the reception operation to the time interval at which the receiver performs the reception operation. Thereby, the intermittent reception operation can be suppressed, for example, when the application is operating in the background. As a result, power consumption related to the reception process can be reduced.

In the information processing device according to the above aspect, the intermittent reception parameter includes a reception interval indicating a time interval at which the receiver performs a reception operation, and the intermittent reception parameter adjustment unit is configured to adjust the reception interval to a first value when the application is operating in the foreground, and adjust the reception interval to a second value larger than the first value when the application is operating in the background. According to this configuration, the intermittent reception operation of the receiver can be controlled by adjusting the reception interval.

In the information processing device according to the above aspect, the intermittent reception parameter includes a reception period indicating a duration of a reception operation performed by the receiver, and the intermittent reception parameter adjustment unit is configured to adjust the reception period to a third value when the application is operating in the foreground, and adjust the reception period to a fourth value smaller than the third value when the application is operating in the background. According to this configuration, the intermittent reception operation of the receiver can be controlled by adjusting the reception period.

In the information processing device according to the above aspect, the intermittent reception parameter includes a reception interval and a reception period, the reception interval indicating a time interval at which the receiver performs a reception operation, the reception period indicating a duration of the reception operation, the intermittent reception parameter adjustment unit is configured to adjust the reception interval to a first value and adjust the reception period to a third value when the application is operating in the foreground, and the intermittent reception parameter adjustment unit is configured to adjust the reception interval to a second value larger than the first value and adjust the reception period to a fourth value smaller than the third value when the application is operating in the background. According to this configuration, the intermittent reception operation of the receiver can be controlled by adjusting the combination of the reception interval and the reception period.

In the information processing device according to the above aspect, the application is configured to estimate a health condition of a user based on a measurement result of a quantity related to information of the user, and the intermittent reception parameter adjustment unit is configured to adjust the intermittent reception parameter so that when the application estimates that the health condition of the user is bad, the duty ratio is smaller than when the application estimates that the health condition of the user is good.

According to the above configuration, when the user's health condition is bad (unhealthy), for example, the intermittent reception operation of the receiver can be controlled so that the measurement result obtained by the measuring device can be received immediately after the measurement.

The information processing device according to the above aspect further includes a reception processing unit configured to calculate a transmission interval based on a result of reception of the packet by the receiver, the transmission interval indicating a time interval at which the packet is transmitted, and the intermittent reception parameter adjustment unit is configured to adjust the intermittent reception parameter based further on the calculated transmission interval.

According to the above configuration, it is possible to prevent a situation where a packet cannot be received, for the reason that the reception interval of the receiver matches the transmission interval of an external device, or for some other reasons.

According to the present invention, an information processing device and a receiving method that can reduce power consumption related to a process of receiving information transmitted from an external device through one-way communication, can be provided.

BRIEF DESCRIPTION OF THE DRAWINGS

FIG. 1 is a block diagram illustrating a configuration example of an information management system according to an embodiment of the present invention.

FIG. 2 is a block diagram illustrating an example of a hardware configuration of a measuring device shown in FIG. 1.

FIG. 3 is a block diagram illustrating an example of a hardware configuration of an information management device shown in FIG. 1.

FIG. 10 is a flowchart illustrating an example of an intermittent reception parameter adjustment operation according to the embodiment.

DETAILED DESCRIPTION

Figure 4:
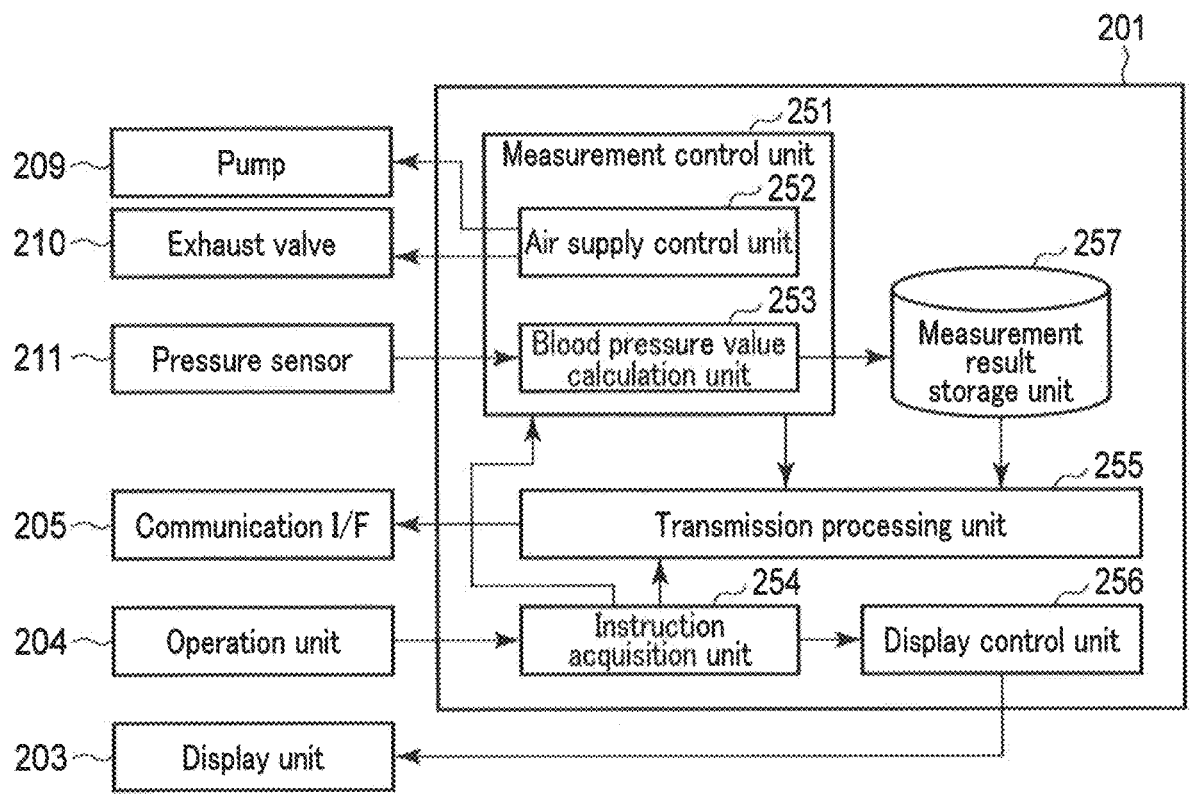
FIG. 4 is a block diagram illustrating an example of a software configuration of the measuring device shown in FIG. 1.

Hereinafter, embodiments of the present invention will be described with reference to the drawings.

According to one embodiment, there is provided an information processing device and a receiving method that can reduce power consumption related to a process of receiving information transmitted from an external device through one-way communication.

§ 1 Application Example

An application example of the present invention will be described with reference to FIG. 1. FIG. 1 illustrates an information management system 10 according to an embodiment. As illustrated in FIG. 1, the information management system 10 includes a measuring device 20 and an information management device 30. The information management device 30 corresponds to the information processing device of the present invention. In this application example, the measuring device 20 is, for example, a wearable device attached to a user, and the information management device 30 is, for example, a mobile terminal owned by the user. The mobile terminal may be, for example, a smartphone, a mobile phone, a tablet PC (personal computer), a laptop PC, or the like.

The measuring device 20 includes a sensor 21 and measures a quantity related to information on the user (hereinafter referred to as "user information") by using the sensor 21. The user information includes, for example, at least one of biological information or activity information of the user. The biological information refers to information obtained from the user's body. Examples of the quantity related to the biological information include blood pressure, pulse rate, heart rate, electrocardiogram, body temperature, arterial oxygen saturation, and blood alcohol concentration. The activity information refers to information indicating physical activity of the user. Examples of the quantity related to the activity information (also referred to as an "activity quantity") include the number of steps, the number of steps going up stairs, and the calorie consumption.

Various types of sensors 21 are used according to the type of user information to be measured. When measuring a blood pressure value, a pressure sensor, a photoelectric sensor, an ultrasonic sensor, an electrode, or the like is used as the sensor 21. Also, when measuring the number of steps, an acceleration sensor or the like is used as the sensor 21. In the present embodiment, a case where the measuring device 20 measures a quantity related to one type of user information (e.g., blood pressure) will be described to simplify the description. However, it should be noted that the measuring device 20 may measure quantities related to multiple types of user information (e.g., a combination of blood pressure and the number of steps).

The measuring device 20 further includes a measurement control unit 22, a transmission processing unit 23, a transmitter 24, and a measurement result storage unit 25. The measurement control unit 22 measures the quantity related to the user information using the sensor 21 and generates a measurement result indicating the measured quantity related to the user information. The measurement control unit 22 stores the generated measurement result in the measurement result storage unit 25. The measurement result is typically associated with measurement time information indicating measurement time.

The transmission processing unit 23 performs a process for transmitting the measurement result. Specifically, the transmission processing unit 23 reads the measurement result to be transmitted from the measurement result storage unit 25, generates a packet including the measurement result, and sends the packet to the transmitter 24. The transmitter 24 includes one or more antennas and wirelessly transmits packets at a predetermined transmission interval. The transmission interval may be variable. The transmitter 24 is a transmitter that periodically transmits a radio signal to the surroundings, which is also referred to as a "beacon terminal" or the like. The transmitter 24 may conform to a short-range communication standard such as Bluetooth or BLE (Bluetooth Low Energy).

The information management device 30 manages the measurement result obtained by the measuring device 20, and includes a receiver 31, a reception processing unit 32, an application execution unit 33, an intermittent reception parameter adjustment unit 34, a measurement result storage unit 35, and an application storage unit 36.

The information management device 30 typically includes a transceiver conforming to a wireless communication standard that is the same as or compatible with that of the transmitter 24 of the measuring device 20, and the receiver 31 is a part of the transceiver. The receiver 31 includes one or more antennas and intermittently receives packets from the measuring device 20. Specifically, the receiver 31 repeats a reception operation for performing packet reception and a pause operation for pausing packet reception. The interval between adjacent reception operations is referred to as a "reception interval", and the duration of each reception operation is referred to as a "reception period". The reception interval and the reception period are intermittent reception parameters for controlling the intermittent reception operation of the receiver 31. The receiver 31 receives a packet from the measuring device 20 and sends the received packet to the reception processing unit 32.

The reception processing unit 32 extracts the measurement result from the packet and stores the measurement result in the measurement result storage unit 35. Since the measuring device 20 transmits the same measurement result many times, the reception processing unit 32 may obtain the same measurement result as that already obtained. In this case, the reception processing unit 32 discards the redundant measurement results obtained, without storing them in the measurement result storage unit 35.

The application storage unit 36 stores a program of an application installed in the information management device 30. For example, the application storage unit 36 stores a program of a health management application that processes the measurement result stored in the measurement result storage unit 35. The health management application may be preinstalled in the information management device 30, downloaded via a network such as the Internet, or provided through a non-transitory computer-readable recording medium such as a CD-ROM. The application execution unit 33 executes an application stored in the application storage unit 36.

The intermittent reception parameter adjustment unit 34 adjusts the intermittent reception parameter depending on whether the health management application is operating in the background or the foreground. An application operating in the foreground indicates an active state in which a user can operate or control the application. An application operating in the background indicates a state in which the application is running but a user cannot operate or control the application. Specifically, the intermittent reception parameter adjustment unit 34 adjusts an intermittent reception parameter so that the duty ratio of the intermittent reception operation (i.e., the ratio of the reception period to the reception interval) is smaller when the health management application is operating in the background than when the health management application is operating in the foreground. In the present embodiment, the intermittent reception parameter adjustment unit 34 adjusts the reception interval. Specifically, the intermittent reception parameter adjustment unit 34 adjusts the reception interval to a first value when the health management application is operating in the foreground, and adjusts the reception interval to a second value that is larger (longer) than the first value when the health management application is operating in the background. Thereby, the reception interval when the health management application is operating in the background is longer than the reception interval when the health management application is operating in the foreground. In other words, when the health management application is operating in the background, the duration of the pause operation is increased. As a result, although it is difficult for the information management device 30 to receive a packet from the measuring device 20, the power consumption related to the reception process can be reduced.

In general, when the health management application is operating in the foreground, it is highly likely that the user is viewing the measurement result on the information management device 30. In this case, it is desirable that the measurement result obtained by the measuring device 20 be immediately taken into the mobile terminal when the measurement result is obtained, so that the measurement result can be viewed on the information management device 30 immediately after the measurement. On the other hand, when the health management application is operating in the background, the user does not view the measurement result on the information management device 30; therefore, the measurement result obtained by the measuring device 20 need not be immediately taken into the information management device 30. As such, when the health management application is operating in the background, the reception interval can be increased.

Hereinafter, the measuring device 20 and the information management device 30 will be described in more detail. In the example described below, the measuring device 20 is a wristwatch-type blood pressure monitor, and measures blood pressure on a wrist as a measurement site. The measurement site is not limited to a wrist, and may be another site such as an upper arm.

§ 2 Configuration Example (Hardware Configuration)
<Measuring Device>

FIG. 2 illustrates an example of a hardware configuration of the measuring device 20. As illustrated in FIG. 2, the measuring device 20 includes a controller 201, a storage unit 202, a display unit 203, an operation unit 204, a communication interface 205, a battery 206, and a blood pressure measuring unit 207.

The controller 201 includes a CPU (central processing unit), a RAM (random access memory), a ROM (read only memory), and the like, and controls each component according to information processing. The storage unit 202 is, for example, an auxiliary storage device such as a semiconductor memory (e.g., a flash memory). The storage unit 202 stores a blood pressure measurement program executed by the controller 201, measurement result data indicating a blood pressure value calculated by the controller 201, and the like. The blood pressure measurement program is a program which causes the measuring device 20 to measure user's blood pressure.

The display unit 203 displays information such as a measurement result. Examples of the display unit 203 include a liquid crystal display (LCD), an organic light emitting diode (OLED) display, and the like. The operation unit 204 allows a user to input an instruction given to the measuring device 20. The operation unit 204 provides an instruction signal corresponding to an operation by the user to the controller 201. The operation unit 204 includes, for example, a plurality of push buttons. A touch screen may be used as a combination of the display unit 203 and the operation unit 204.

Figure 5:
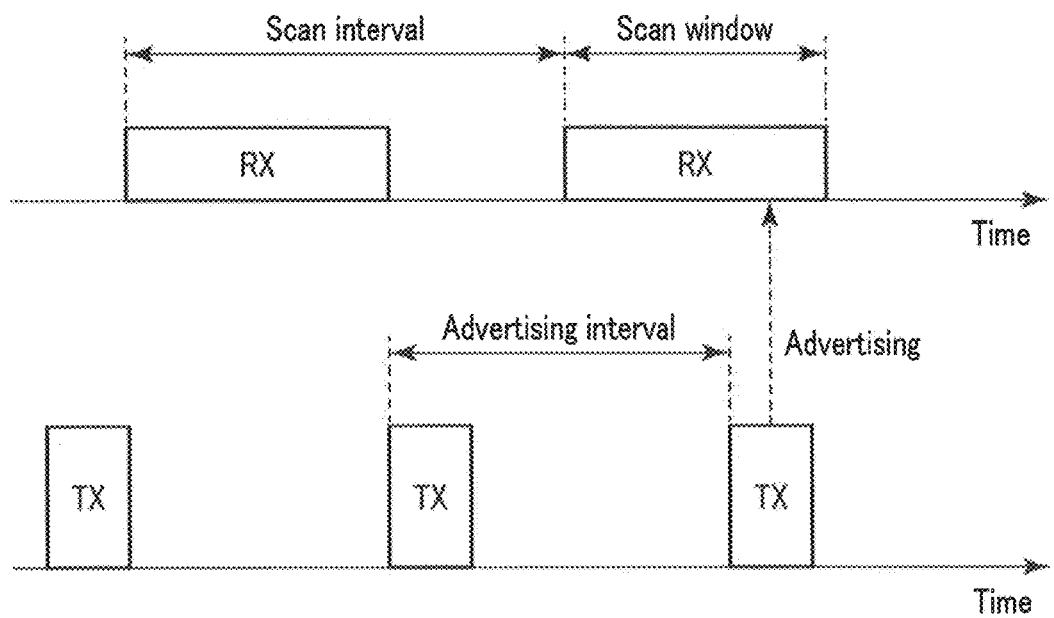
FIG. 5 is a diagram illustrating advertising performed in BLE.

The communication interface 205 is an interface for communicating with an external device. In the present embodiment, the communication interface 205 includes only a transmitter that broadcasts a radio signal at a predetermined transmission interval. Namely, the communication interface 205 has a transmission function but does not have a reception function. The transmitter performs processing including up-conversion and amplification. A transmitter with low power consumption is desirable. In the present embodiment, the communication interface 205 conforms to BLE, and uses a communication method called advertising that broadcasts a signal without connecting to a network. The above transmission interval corresponds to an advertising interval as in BLE. As illustrated in FIG. 5, the advertising interval refers to a time interval at which advertising communication is performed. The advertising interval can be set in units of 0.625 [ms] in the range of 20 [ms] to 10.24 [s]. For the advertising communication, three channels called "advertising channels" are used. In one advertising communication, signals are transmitted using the three channels sequentially.

In another embodiment, the communication interface 205 may further include a communication module that allows for bidirectional communication. The communication module may be a wireless communication module, a wired communication module, or a combination of a wireless communication module and a wired communication module.

The battery 206 is, for example, a rechargeable secondary battery. The battery 206 supplies power to each component in the measuring device 20. The battery 206 supplies power to the controller 201, the storage unit 202, the display unit 203, the operation unit 204, the communication interface 205, and the blood pressure measuring unit 207, for example.

The blood pressure measuring unit 207 measures user's blood pressure. In the example shown in FIG. 2, the blood pressure measuring unit 207 includes a cuff 208, a pump 209, an exhaust valve 210, and a pressure sensor 211. The cuff 208 includes an air bag, and the air bag is connected to the pump 209 and the exhaust valve 210 via an air passage 212. The pump 209 supplies the air to the air bag of the cuff 208. When the air is supplied to the air bag by the pump 209, the air bag expands. Due to the expansion of the air bag, the cuff 208 presses the measurement site (the wrist in this example). The exhaust valve 210 is provided to exhaust the air from the air bag of the cuff 208. Driving of the pump 209 and the opening and closing of the exhaust valve 210 are controlled by the controller 201. The pressure sensor 211 detects the pressure inside the cuff 208 and outputs a pressure signal indicating the detected pressure to the controller 201. The controller 201 calculates a blood pressure value based on the pressure signal received from the pressure sensor 211. The blood pressure value includes, but is not limited to, systolic blood pressure (SBP) and diastolic blood pressure (DBP).

Although not shown in FIG. 2, an amplifier that amplifies the output signal of the pressure sensor 211, and an analog-to-digital converter that converts the output signal of the amplifier from an analog signal to a digital signal are provided between the pressure sensor 211 and the controller 201.

In regard to the specific hardware configuration of the measuring device 20, a component can be omitted, replaced, or added as appropriate according to the embodiment. For example, the controller 201 may include a plurality of processors.

<Information Management Device>

FIG. 3 illustrates an example of a hardware configuration of the information management device 30. As illustrated in FIG. 3, the information management device 30 includes a controller 301, a storage unit 302, a display unit 303, an operation unit 304, a communication interface 305, and a battery 306.

The controller 301 includes a CPU, a RAM, a ROM, and the like, and controls each component according to information processing. The storage unit 302 is, for example, an auxiliary storage device such as a hard disk drive (HDD) or a semiconductor memory (e.g., a solid state drive (SSD)). The storage unit 302 stores an information management program executed by the controller 301, measurement result data received from the measuring device 20, and the like. The information management program is a program which causes the measuring device 20 to manage the measurement result.

A combination of the display unit 303 and the operation unit 304 is realized by a touch screen. The touch screen may be either a pressure-sensitive type (resistance type) or a proximity type (capacitance type). Examples of the display unit 303 include an LCD, an OLED display, and the like. The operation unit 304 allows a user to input an instruction given to the information management device 30. The operation unit 304 provides an instruction signal corresponding to an operation by the user to the controller 301. The operation unit 304 may further include a plurality of push buttons. The display unit 303 and the operation unit 304 may be realized as separate devices.

The communication interface 305 is an interface for communicating with an external device. The communication interface 305 includes a wireless communication module corresponding to a wireless communication standard that is the same as or compatible with that of the communication interface 205 of the measuring device 20. The wireless communication module performs processing including amplification and down-conversion on the received signal. In the present embodiment, the communication interface 305 includes a BLE communication module. As illustrated in FIG. 5, the BLE communication module performs reception operations at a reception interval called a scan interval, and each reception operation continues for a duration called a scan window. The scan interval and the scan window can be set in the range of 2.5 [ms] to 10.24 [s].

The communication interface 305 may further include another wireless communication module. For example, the communication interface 305 includes a Wi-Fi (registered trademark) module, is connected to a network (e.g., the Internet) via a Wi-Fi base station, and communicates with an external device via the network. The communication interface 305 may further include a wired communication module. For example, the communication interface 305 may include a USB connector and be connected to an external device via a USB cable.

The battery 306 is, for example, a rechargeable secondary battery. The battery 306 supplies power to each component in the information management device 30. The battery 306 supplies power to the controller 301, the storage unit 302, the display unit 303, the operation unit 304, and the communication interface 305, for example.

In regard to the specific hardware configuration of the information management device 30, a component can be omitted, replaced, or added as appropriate according to the embodiment. For example, the controller 301 may include a plurality of processors. Also, the information management device 30 may be realized by a plurality of information processing devices (computers).

(Software Configuration)

<Measuring Device>

An example of a software configuration of the measuring device 20 will be described with reference to FIG. 4.

The controller 201 (FIG. 2) of the measuring device 20 loads, to the RAM, the blood pressure measurement program stored in the storage unit 202. Then, with the CPU, the controller 201 interprets and executes the blood pressure measurement program loaded to the RAM, and controls each component. Thereby, the measuring device 20 functions as a computer that includes a measurement control unit 251, an instruction acquisition unit 254, a transmission processing unit 255, a display control unit 256, and a measurement result storage unit 257, as illustrated in FIG. 4. The measurement result storage unit 257 is realized by the storage unit 202.

The measurement control unit 251 measures user's blood pressure. In one example, the measurement control unit 251 starts measurement when the conditions under which measurement of blood pressure is recommended are satisfied. The conditions include, for example, the current time becoming a preset time (e.g., 7:30 and 22:30). In another example, the measurement control unit 251 starts measurement in response to a user operation.

The measurement control unit 251 includes an air supply control unit 252 and a blood pressure value calculation unit 253. The air supply control unit 252 controls supply of a fluid to the cuff 208. Specifically, the air supply control unit 252 controls the driving of the pump 209, and the opening and closing of the exhaust valve 210. The blood pressure value calculation unit 253 calculates a blood pressure value by the oscillometric method, based on the pressure signal received from the pressure sensor 211 in the pressurizing process for supplying the air to the cuff 208 or the depressurizing process for exhausting the air from the cuff 208. A pulse rate may also be calculated simultaneously with the blood pressure value. The blood pressure value calculation unit 253 stores, in the measurement result storage unit 257, the measurement result indicating the calculated blood pressure value in association with the measurement time information.

The instruction acquisition unit 254 acquires an instruction input by the user who is using the operation unit 204. Examples of the instruction include an instruction to start measurement, an instruction for viewing the measurement result history, and the like. When the instruction acquisition unit 254 acquires an instruction to start measurement, the instruction acquisition unit 254 gives the instruction to the measurement control unit 251. When the instruction acquisition unit 254 acquires an instruction to view the history, the instruction acquisition unit 254 gives the instruction to the display control unit 256.

The display control unit 256 controls the operation of the display unit 203. The display control unit 256 changes the display content in response to a user operation. Also, immediately after a new measurement result is obtained, the display control unit 256 causes the display unit 203 to display the new measurement result.

The transmission processing unit 255 selects a plurality of measurement results to be transmitted from among a plurality of measurement results stored in the measurement result storage unit 257, generates one or more packets to which the selected measurement results are allocated, and transmits the generated packet(s) via the communication interface 205. The transmission processing unit 255 may select one measurement result to be transmitted from among a plurality of measurement results stored in the measurement result storage unit 257, and generate and transmit a packet including the selected measurement result.

The transmission operation of the transmission processing unit 255 will be described with the use of a specific example. In this example, it is assumed that three measurement results, which are a measurement result 1, a measurement result 2, and a measurement result 3, are transmitted. The transmission processing unit 255 generates three packets: a packet 1 including the measurement result 1; a packet 2 including the measurement result 2; and a packet 3 including the measurement result 3. The transmission processing unit 255 repeats the operation of transmitting the packet 1, the packet 2, and the packet 3 in the mentioned order. Namely, the transmission processing unit 255 sequentially transmits the packet 1, the packet 2, and the packet 3, as in "packet 1, packet 2, packet 3, packet 1, packet 2, packet 3, packet 1, . . . ". In this manner, the measuring device 20 repeatedly transmits a plurality of measurement results.

In some cases, a plurality of measurement results can be included in each packet. If two measurement results are to be included in each packet, the transmission processing unit 255 may generate two packets, such as a packet 1 including the measurement result 1 and the measurement result 2, and a packet 2 including the measurement result 1 and the measurement result 3. In another example, the transmission processing unit 23 may generate three packets, such as a packet 1 including the measurement result 1 and the measurement result 2, a packet 2 including the measurement result 1 and the measurement result 3, and a packet 3 including the measurement result 2 and the measurement result 3. The transmission processing unit 255 may generate one packet including the measurement result 1, the measurement result 2, and the measurement result 3.

In the information management system 10, there may occur a situation where the information management device 30 fails to receive a packet from the measuring device 20. This situation occurs, for example, because the information management device 30 is away from the measuring device 20, the information management device 30 is turned off, or the wireless communication function of the information management device 30 is turned off. If the measuring device 20 is to transmit only a measurement result obtained by a first measurement in a period between the first measurement and a subsequent second measurement (in this case, only a measurement result obtained by the second measurement is transmitted in a period between the second measurement and a subsequent third measurement), unless the information management device 30 successfully receives the measurement result from the measuring device 20 during this period, the opportunity for the information management device 30 to receive the measurement result is lost. In some cases, the occurrence of a certain amount of data loss in the information management device 30 is acceptable; however, in many cases it is desired that the information management device 30 receive all the measurement results obtained by the measuring device 20.

In the present embodiment, the measuring device 20 transmits a plurality of measurement results including the latest measurement result and the measurement results obtained therebefore, as described above. Accordingly, each measurement result is transmitted over a longer period than when only the latest measurement result is transmitted, so that the possibility of the information management device 30 receiving each measurement result is increased. As a result, occurrences of data loss at the information management device 30 can be reduced.

The advertisement of BLE will be schematically described below.

In the passive scanning method employed in BLE, a new node periodically transmits an advertisement packet that informs its existence, as illustrated in FIG. 5. The new node can save power consumption by entering a sleep state in a period from the transmission of the advertisement packet to the next transmission of the advertisement packet. Further, since a receiver of the advertisement packet also operates intermittently, the power consumption associated with the transmission and reception of the advertisement packet is very small.

Figure 6:
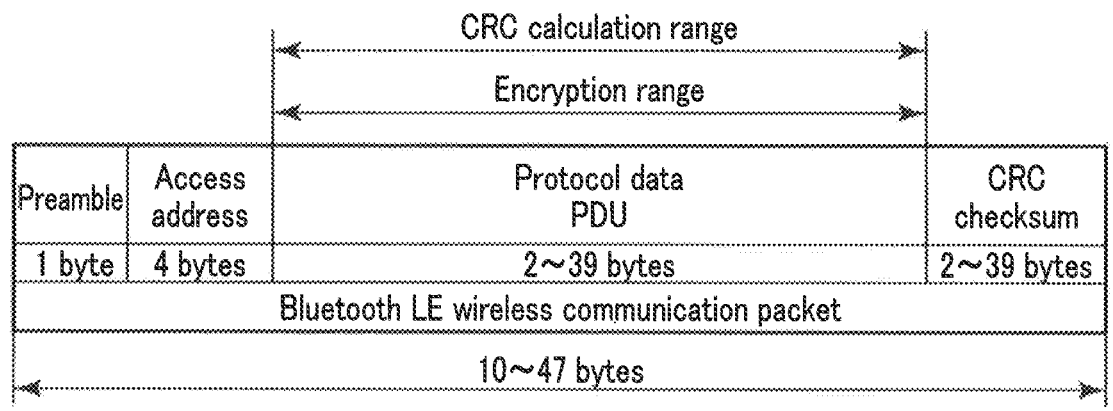
FIG. 6 is a diagram illustrating a data structure of a packet exchanged in BLE.

FIG. 6 shows a basic structure of a BLE wireless communication packet. A BLE wireless communication packet includes a 1-byte preamble, a 4-byte access address, a 2- to 39-byte (variable) protocol data unit (PDU), and a 3-byte cyclic redundancy checksum (CRC). The length of the BLE wireless communication packet depends on the length of the PDU and is 10 to 47 bytes.

The preamble field is prepared for synchronization of BLE wireless communication and stores repetition of "01" or "10". The access address stores a fixed numerical value in the advertising channel and a random access address in the data channel. In the present embodiment, an advertisement packet, which is a BLE wireless communication packet transmitted on the advertising channel, is targeted. The CRC field is used to detect reception errors. The calculation range of the CRC is only the PDU field.

Figure 7:
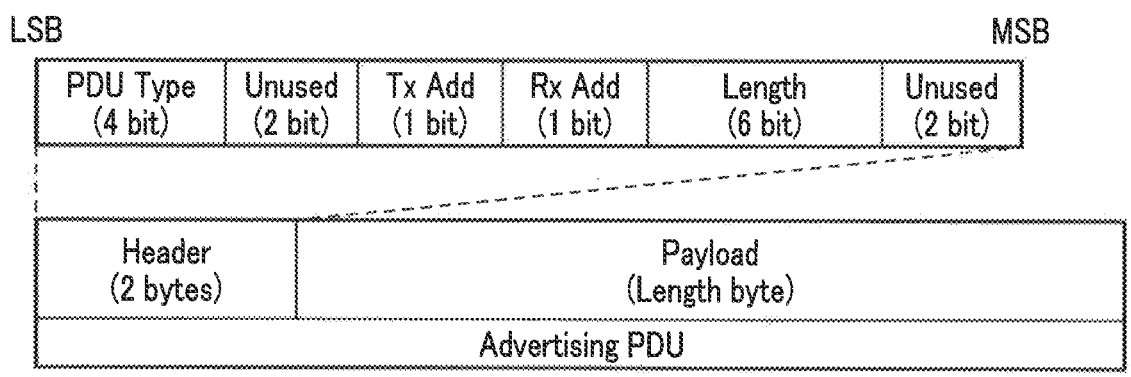
FIG. 7 is a diagram illustrating a data structure of a PDU field of an advertisement packet.

Next, the PDU field of the advertisement packet will be described with reference to FIG. 7. The PDU field of the data communication packet, which is a BLE wireless communication packet transmitted on the data channel, has a data structure different from that shown in FIG. 7; however, since the data communication packet is not targeted in the present embodiment, a description of the PDU field of the data communication packet is omitted.

The PDU field of the advertisement packet includes a 2-byte header and a 0- to 37-byte (variable) payload. The header further includes a 4-bit PDU Type field, a 2-bit unused field, a 1-bit TxAdd field, a 1-bit RxAdd field, a 6-bit Length field, and a 2-bit unused field.

A value indicating the PDU type is stored in the PDU Type field. Some values of "connectable advertising", "non-connecting advertising", etc., have already been defined. A flag indicating whether or not there is a transmission address in the payload is stored in the TxAdd field. Likewise, a flag indicating whether or not there is a reception address in the payload is stored in the RxAdd field. A value indicating the byte size of the payload is stored in the Length field. Any data can be stored in the payload. Therefore, the measuring device 20 stores the measurement results (SBP and DBP in this example) and the measurement time information in the payload using a predetermined data structure. The payload may further include, for example, an identifier representing the measuring device 20 which is a transmission source device.

In the present embodiment, an example is described in which all the functions of the measuring device 20 are implemented by a general-purpose CPU. However, some or all of the above functions may be implemented by one or more dedicated processors.

<Information Management Device>

Figure 8:
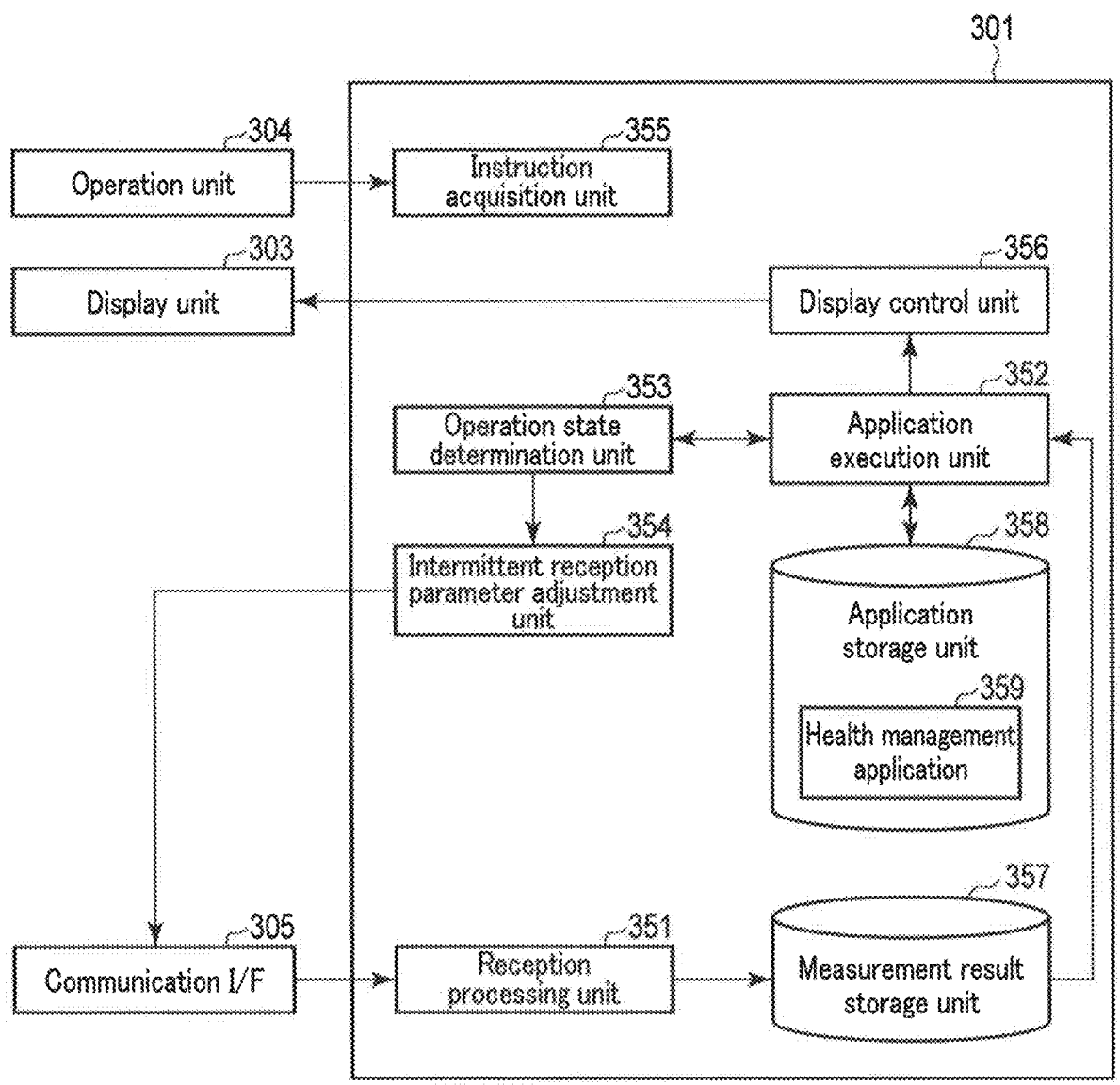
FIG. 8 is a block diagram illustrating an example of a software configuration of the information management device shown in FIG. 1.

An example of a software configuration of the information management device 30 according to the present embodiment will be described with reference to FIG. 8.

The controller 301 (FIG. 3) of the information management device 30 loads, to the RAM, a lifestyle management program stored in the storage unit 302. Then, with the CPU, the controller 301 interprets and executes the lifestyle management program loaded to the RAM, and controls each component. Thereby, the information management device 30 functions as a computer that includes a reception processing unit 351, an application execution unit 352, an operation state determination unit 353, an intermittent reception parameter adjustment unit 354, an instruction acquisition unit 355, a display control unit 356, a measurement result storage unit 357, and an application storage unit 358, as illustrated in FIG. 8. The measurement result storage unit 357 and the application storage unit 358 are realized by the storage unit 302.

The reception processing unit 351 receives a packet from the measuring device 20 via the communication interface 305. The reception processing unit 351 confirms an identifier included in the packet, and discards the received packet if the value of the identifier is inappropriate. If the value of the identifier is appropriate, the reception processing unit 351 extracts the measurement result and measurement time information included in the packet and stores them in the measurement result storage unit 357.

The application storage unit 358 stores programs of applications including a health management application 359. The application execution unit 352 executes the health management application 359. The health management application 359 is an application that processes the measurement result stored in the measurement result storage unit 357. For example, the health management application 359 presents the measurement result to the user in the form of a graph. In addition, the health management application 359 estimates the user's health condition based on the measurement result. For example, the health management application 359 estimates that the user's health condition is good when the SBP is less than a predetermined threshold (e.g., 140 [mmHg]), and determines that the user's health condition is bad (unhealthy) when the SBP is equal to or greater than the threshold. The health condition need not necessarily be represented by categories, and may be represented by a numerical value. The health management application 359 notifies the user of the result of determining the user's health condition.

The operation state determination unit 353 determines the operation state of the health management application 359. Specifically, the operation state determination unit 353 determines whether the health management application 359 is operating in the background or the foreground.

The intermittent reception parameter adjustment unit 354 adjusts an intermittent reception parameter for controlling the intermittent reception operation of the communication interface 305 based on the result of the determination made by the operation state determination unit 353. The intermittent reception parameter includes a reception interval (scan interval) and a reception period (scan window). In the present embodiment, the intermittent reception parameter adjustment unit 354 adjusts the reception interval. For example, the intermittent reception parameter adjustment unit 354 adjusts the reception interval to a first value when the operation state determination unit 353 determines that the health management application 359 is operating in the foreground, and adjusts the reception interval to a second value larger than the first value when the operation state determination unit 353 determines that the health management application 359 is operating in the background. The first value and the second value are variable. For example, the first value and the second value may be changed according to a user operation. The first value and the second value may be changed according to a remaining battery level. The first value and the second value may be fixed values.

The instruction acquisition unit 355 acquires an instruction input by the user who is using the operation unit 204 and passes the instruction to the application execution unit 352. The instruction includes, for example, an instruction for displaying a measurement result. The display control unit 356 controls the operation of the display unit 303. For example, the display control unit 356 generates image data including the graph generated by the health management application 359 and provides the image data to the display unit 303.

In the present embodiment, an example is described in which all the functions of the information management device 30 are realized by a general-purpose CPU. However, some or all of the above functions may be implemented by one or more dedicated processors. Also, some of the above functions may be executed by an operating system (OS) operating on the information management device 30.

§ 3 Operation Example

<Measuring Device>

An operation example of the measuring device 20 according to the present embodiment will be described.

Figure 9:
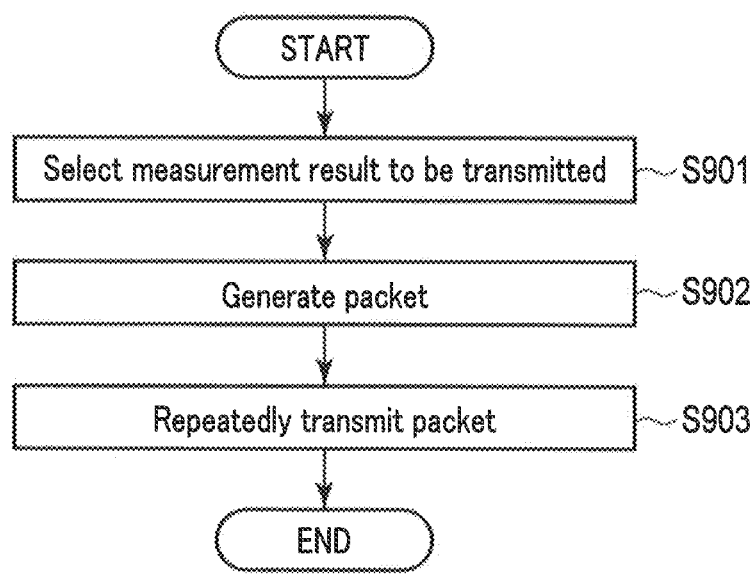
FIG. 9 is a flowchart illustrating an example of a transmission operation according to the embodiment.

FIG. 9 illustrates an example of the transmission operation of the measuring device 20. The transmission operation illustrated in FIG. 9 starts, for example, when a new measurement result is obtained. In step S901 in FIG. 9, the controller 201 of the measuring device 20 functions as the transmission processing unit 255, and selects a plurality of measurement results to be transmitted from among the measurement results stored in the storage unit 202 (specifically, the measurement result storage unit 257). For example, the controller 201 selects a predetermined number of measurement results in order from the newest one.

In step S902, the controller 201 functions as the transmission processing unit 255, and generates a plurality of packets based on the selected measurement results. Each packet includes one or more of the selected measurement results. In step S903, the controller 201 functions as the transmission processing unit 255, and transmits the generated packets. The processing shown in step S903 is continued, for example, until a new measurement result is obtained.

The process described above is merely an example, and each processing may be changed as much as possible. Further, in the process described above, a step can be omitted, replaced, or added as appropriate according to the embodiment.

In the present embodiment, an example is described in which all the functions of the measuring device 20 are realized by a general-purpose CPU. However, some or all of the above functions may be realized by one or more dedicated processors.

<Information Management Device>

An operation example of the information management device 30 according to the present embodiment will be described.

FIG. 10 illustrates an example of the intermittent reception parameter adjustment operation of the information management device 30. In step S1001 in FIG. 10, the controller 301 of the information management device 30 functions as the application execution unit 352, and executes the health management application 359. For example, the controller 301 activates the health management application 359 in response to a user operation, and the health management application 359 operates in the foreground. In step S1002, the controller 301 functions as the operation state determination unit 353, and determines that the health management application 359 is operating in the foreground. In step S1003, the controller 301 functions as the intermittent reception parameter adjustment unit 354, and adjusts the reception interval to a first value $V_1$.

In step S1004, the controller 301 functions as the instruction acquisition unit 355, and determines whether or not the user has performed a transition operation for shifting the health management application 359 from the foreground state to the background state. This transition operation is, for example, an operation for activating another application. The processing of step S1004 is continued until the user performs the transition operation. When the user performs the transition operation, the process proceeds to step S1005.

In step S1005, the controller 301 functions as the operation state determination unit 353, and determines that the health management application 359 is operating in the background. In step S1006, the controller 301 functions as the intermittent reception parameter adjustment unit 354, and adjusts the reception interval to a second value $V_2$. The relationship between $V_1$ and $V_2$ is $V_2 > V_1$.

In step S1007, the controller 301 functions as the instruction acquisition unit 355, and determines whether or not the user has performed a transition operation for shifting the health management application 359 from the background state to the foreground state. The processing of step S1007 is continued until the user performs the transition operation. When the user performs the transition operation, the process returns to step S1002. When the process returns to step S1002, the reception interval is changed from the second value $V_2$ to the first value $V_1$.

The process described above is merely an example, and each processing may be changed as much as possible. Further, in the process described above, a step can be omitted, replaced, or added as appropriate according to the embodiment.

In the present embodiment, an example is described in which all the functions of the information management device 30 are realized by a general-purpose CPU. However, some or all of the above functions may be implemented by one or more dedicated processors.

(Advantageous Effects)

As described above, in the present embodiment, the reception interval of the intermittent reception operation is adjusted so that the reception interval when the health management application 359 is operating in the background is longer than the reception interval when the health management application 359 is operating in the foreground. Thereby, the duty ratio when the health management application 359 is operating in the background is smaller than the duty ratio when the health management application 359 is operating in the foreground. As a result, power consumption related to the reception process can be reduced.

§ 4 Modification

In the present embodiment described above, the intermittent reception parameter adjustment unit 354 adjusts the reception interval. The intermittent reception parameter adjustment unit 354 may adjust the reception period. In this case, the intermittent reception parameter adjustment unit 354 adjusts the reception period to a third value when the operation state determination unit 353 determines that the health management application 359 is operating in the foreground, and adjusts the reception period to a fourth value smaller (shorter) than the third value when the operation state determination unit 353 determines that the health management application 359 is operating in the background. Alternatively, the intermittent reception parameter adjustment unit 354 may adjust a combination of the reception interval and the reception period. In this case, the intermittent reception parameter adjustment unit 354 adjusts the reception interval to the first value and adjusts the reception period to the third value when the operation state determination unit 353 determines that the health management application 359 is operating in the foreground; and the intermittent reception parameter adjustment unit 354 adjusts the reception interval to the second value larger than the first value, and adjusts the reception period to the fourth value smaller than the third value when the operation state determination unit 353 determines that the health management application 359 is operating in the background. The third value and the fourth value may be variable or fixed values. In these cases as well, power consumption related to the reception process can be reduced as in the present embodiment described above.

The intermittent reception parameter adjustment unit 354 may adjust the intermittent reception parameters based on the operation state of the health management application 359 and the user's health condition estimated by the health management application 359. For example, when the health management application 359 determines that the user's health condition is good, the intermittent reception parameter adjustment unit 354 adjusts the intermittent reception parameters according to the operation state of the health management application 359 as described above; and when the health management application 359 determines that the user's health condition is bad, the intermittent reception parameter adjustment unit 354 adjusts the intermittent reception parameters regardless of the operation state of the health management application 359. Specifically, the intermittent reception parameter adjustment unit 354 adjusts the reception interval to a value smaller than the second value when the health management application 359 determines that the user's health condition is bad. Alternatively or additionally, the intermittent reception parameter adjustment unit 354 adjusts the reception period to a value larger than the fourth value when the health management application 359 determines that the user's health condition is bad. Thereby, when the health management application 359 determines that the user's health condition is bad, the information management device 30 can easily receive the measurement result obtained by the measuring device 20 after the determination. As a result, as soon as the measurement result is obtained by the measuring device 20, the health management application 359 can make a notification such as a warning based on the measurement result.

The intermittent reception parameter adjustment unit 354 may adjust the intermittent reception parameters based on the operation state of the health management application 359 and the transmission interval of the measuring device 20. For example, the communication interface 205 temporarily performs a continuous reception operation in which the reception interval is equal to the reception period, and the reception processing unit 351 calculates the transmission interval of the measuring device 20 based on the interval between the packets received from the measuring device 20. For example, when the reception interval of the information management device 30 is equal to or an integral multiple of the transmission interval of the measuring device 20, the information management device 30 may not be able to receive a packet from the measuring device 20. By adjusting the intermittent reception parameters based on the transmission interval of the measuring device 20, it is possible to prevent a situation in which the information management device 30 cannot receive a packet from the measuring device 20.

The health management application 359 is not always activated. When the health management application 359 is not activated, the intermittent reception parameter adjustment unit 354 makes the reception interval the same as or longer than the reception interval for the case where the health management application 359 is operating in the background. Alternatively or additionally, when the health management application 359 is not activated, the intermittent reception parameter adjustment unit 354 makes the reception period the same as or shorter than the reception period for the case where the health management application 359 is operating in the background. Alternatively, when the health management application 359 is not activated, the controller 301 may turn off the BLE communication module of the communication interface 305.

In the present embodiment described above, the measuring device 20 measures blood pressure using the oscillometric method. The measuring device 20 may measure blood pressure by other methods. Also, the measuring device 20 may be a blood pressure measuring device that can obtain a blood pressure value on a beat-by-beat basis. For example, the measuring device 20 may measure blood pressure by the tonometry method. The measuring device 20 may detect a pulse transit time (PTT), which is a propagation time of a pulse wave propagating through an artery, by using two or more electrodes, and estimate a blood pressure value (e.g., SBP and DBP) based on the detected pulse transit time. Also, the measuring device 20 may measure a volume pulse wave optically and estimate a blood pressure value based on the measurement result. Furthermore, the measuring device 20 may measure blood pressure using ultrasonic waves.

Information stored in the payload of the packet may be encrypted. As an example, the measuring device 20 displays an encryption key used for encryption on the display unit 203, and the user checks the encryption key and inputs it to the information management device 30 using the operation unit 304. The controller 301 of the information management device 30 decrypts the payload portion of the packet using the encryption key. Thereby, the measurement result can be transmitted from the measuring device 20 to the information management device 30 without fear of information leakage. The encryption key may be changed periodically.

The quantity (physical quantity, etc.) to be measured is not limited to the quantity related to user information. For example, the quantity to be measured may be a quantity related to the environment such as a temperature or radiation dose.

The measuring device 20 is an example of an external device. The external device need not have a measurement function. Therefore, the information included in the packet transmitted from the external device to the information management device 30 need not necessarily be a measurement result, and may in fact be any information.

In short, the present invention is not limited to the above-described embodiments and can be embodied in practice by modifying the structural elements without departing from the gist of the invention. In addition, various inventions can be made by suitably combining the structural elements disclosed in connection with the above embodiments. For example, some of the structural elements may be deleted from the entire structural elements described in the embodiments. Furthermore, structural elements of different embodiments may be appropriately combined.

A part or whole of the above-described embodiments may be described as indicated in the appendices below, but is not limited thereto.

APPENDIX 1

An information processing device comprising:
a receiver configured to receive a packet for one-way communication;
a processor; and
a memory connected to the processor,
wherein the processor is configured to:
execute an application, and
adjust an intermittent reception parameter for controlling an intermittent reception operation of the receiver so that when the application is operating in a background, a duty ratio of the intermittent reception operation is smaller than when the application is operating in a foreground.

APPENDIX 2

A receiving method performed by an information processing device, the method comprising:
receiving, by a receiver, a packet for one-way communication;
executing, by at least one processor, an application; and
adjusting, by at least one processor, an intermittent reception parameter for controlling an intermittent reception operation so that when the application is operating in a background, a duty ratio of the intermittent reception operation of the receiver is smaller than when the application is operating in a foreground.

REFERENCE SIGNS LIST

10. Information management system
20. Measuring device
21. Sensor
22. Measurement control unit
23. Transmission processing unit
24. Transmitter
25. Measurement result storage unit
201. Controller
202. Storage unit
203. Display unit
204. Operation unit
205. Communication interface
206. Battery
207. Blood pressure measuring unit
208. Cuff
209. Pump
210. Exhaust valve
211. Pressure sensor
212. Air passage
251. Measurement control unit
252. Air supply control unit
253. Blood pressure value calculation unit
254. Instruction acquisition unit
255. Transmission processing unit
256. Display control unit
257. Measurement result storage unit
30. Information management device
31. Receiver
32. Reception processing unit
33. Application execution unit
34. Intermittent reception parameter adjustment unit
35. Measurement result storage unit
36. Application storage unit
301. Controller
302. Storage unit
303. Display unit
304. Operation unit
305. Communication interface
306. Battery
351. Reception processing unit
352. Application execution unit
353. Operation state determination unit
354. Intermittent reception parameter adjustment unit
355. Instruction acquisition unit
356. Display control unit
357. Measurement result storage unit
358. Application storage unit
359. Health management application

The invention claimed is:

1. An information processing device comprising:
a receiver configured to receive a packet for one-way communication including data; and
a processor coupled to the receiver, the processor being configured to:
acquire the packet for one-way communication received by the receiver;
execute an application that processes the data included in the packet for one-way communication; and
adjust an intermittent reception parameter for controlling an intermittent reception operation of the receiver so that: when the application is operating in a background, a duty ratio of the intermittent reception operation of the receiver is smaller than when the application is operating in a foreground; and when the application is not running, the duty ratio is smaller than when the application is operating in the background,
wherein the application operating in the background indicates that the application is running but is in a noncontrollable state, and the application operating in the foreground indicates that the application is in a controllable state.

2. The information processing device according to claim 1, wherein:
the intermittent reception parameter includes a reception interval indicating a time interval at which the receiver performs a reception operation; and
the processor is configured to adjust the reception interval to a first value when the application is operating in the foreground, and adjust the reception interval to a second value larger than the first value when the application is operating in the background.

3. The information processing device according to claim 1, wherein:
the intermittent reception parameter includes a reception period indicating a duration of a reception operation performed by the receiver; and
the processor is configured to adjust the reception period to a third value when the application is operating in the foreground, and adjust the reception period to a fourth value smaller than the third value when the application is operating in the background.

4. The information processing device according to claim 1, wherein:
the intermittent reception parameter includes a reception interval and a reception period, the reception interval indicating a time interval at which the receiver performs a reception operation, the reception period indicating a duration of the reception operation;
the processor is configured to adjust the reception interval to a first value and adjust the reception period to a third value when the application is operating in the foreground; and
the processor is configured to adjust the reception interval to a second value larger than the first value and adjust the reception period to a fourth value smaller than the third value when the application is operating in the background.

5. The information processing device according to claim 1, wherein:
the packet for one-way communication includes, as the data, a measurement result of a quantity related to information of a user;
the application is configured to estimate a health condition of the user based on the measurement result; and
the processor is configured to adjust the intermittent reception parameter so that when the application estimates that the health condition of the user is bad, the duty ratio is smaller than when the application estimates that the health condition of the user is good.

6. The information processing device according to claim 1, wherein:
the processor is further configured to calculate a transmission interval based on a result of reception of the packet by the receiver, the transmission interval indicating a time interval at which the packet is transmitted; and
the processor is configured to adjust the intermittent reception parameter based further on the calculated transmission interval.

7. A receiving method performed by an information processing device comprising a receiver and a processor coupled to the receiver, the method comprising:
receiving, by the receiver, a packet for one-way communication including data;
acquiring, by the processor, the packet for one-way communication received by the receiver;
executing, by the processor, an application that processes the data included in the packet for one-way communication; and
adjusting, by the processor an intermittent reception parameter for controlling an intermittent reception operation of the receiver so that: when the application is operating in a background, a duty ratio of the intermittent reception operation of the receiver is smaller than when the application is operating in a foreground; and when the application is not running, the duty ratio is smaller than when the application is operating in the background,
wherein the application operating in the background indicates that the application is running but is in a noncontrollable state, and the application operating in the foreground indicates that the application is in a controllable state.

8. A non-transitory computer readable medium including computer executable instructions, wherein the instructions, when executed by a processor, cause the processor to perform a method comprising:
acquiring a packet for one-way communication including data, the packet for one-way communication being received by a receiver coupled to the processor;
executing an application that processes the data included in the packet for one-way communication; and
adjusting an intermittent reception parameter for controlling an intermittent reception operation of the receiver so that: when the application is operating in a background, a duty ratio of the intermittent reception operation of the receiver is smaller than when the application is operating in a foreground; and when the application is not running, the duty ratio is smaller than when the application is operating in the background,
wherein the application operating in the background indicates that the application is running but is in a noncontrollable state, and the application operating in the foreground indicates that the application is in a controllable state.

* * * * *